United States Patent [19]
Diehl et al.

[11] Patent Number: 5,032,687
[45] Date of Patent: Jul. 16, 1991

[54] PROCESS FOR THE PREPARATION OF CYCLOPROPYLAMINE

[75] Inventors: Herbert Diehl, Leverkusen; Heinz U. Blank, Odenthal-Gloebusch; Edwin Ritzer, Gladbeck, all of Fed. Rep. of Germany

[73] Assignee: Kernforschunganlage Julich Gesellschaft mit beschränkter Haftung., Julich, Fed. Rep. of Germany

[21] Appl. No.: 423,069

[22] Filed: Oct. 18, 1989

[30] Foreign Application Priority Data

Oct. 29, 1988 [DE] Fed. Rep. of Germany ....... 3836917

[51] Int. Cl.$^5$ .................... C07C 209/56; C07C 209/58
[52] U.S. Cl. ......................................... 564/1; 564/414; 564/448; 564/488
[58] Field of Search .................... 564/1, 448, 414, 488

[56] References Cited

U.S. PATENT DOCUMENTS 3,711,549  1/1973  Phillips et al. ......................... 564/1

FOREIGN PATENT DOCUMENTS 1939759  3/1970  Fed. Rep. of Germany .
2093472  1/1972  France .
1257097  12/1971  United Kingdom .

OTHER PUBLICATIONS

Roger Adams "Organic Reactions" vol. III, pp. 265–270, 280–283, 288, 1946, John Wiley & Sons, New York, U.S.A. E. S. Wallis et al.: The Hofmann Reaction.

Justas Liebigs Annalen Der Chemie, vol. 499, pp. 1–25, 1932 Verlag Chemie, Weinheim/Bergstr. und Berlin, DE; P. Lipp et al.: "Studien in der Cyclopropan-Reihe, Cyclopropanon" *pp. 12–14*.

Primary Examiner—Glennon H. Hollrah
Assistant Examiner—Scott C. Rand
Attorney, Agent, or Firm—Frishauf, Holtz, Goodman & Woodward

[57] ABSTRACT

The present process for the preparation of cyclopropylamine by the so-called Hofmann degradation of cyclopropanecarboxamide is characterized in that the cyclopropanecarboxamide is employed in the form of a solution. The new process can be carried out at 5°–35° C. The cyclopropylamine is obtained after introducing the reaction mixture into a concentrated alkali metal hydroxide solution.

6 Claims, No Drawings

PROCESS FOR THE PREPARATION OF CYCLOPROPYLAMINE

BACKGROUND OF THE INVENTION

The present invention relates to a process for the preparation of cyclopropylamine from cyclopropanecarboxamide by the so-called Hofmann degradation.

Cyclopropylamine is an important intermediate in the preparation of biologically active substances.

The so-called Hofmann degradation, the rearrangement of acid amides with decarboxylation to give primary amines, is known in principle. This process has also already been used for the preparation of cyclopropylamine (DE-OS (German Published Specification) 1,939,759). In this, sodium hypochlorite solution is added at 0° C. to a suspension of the cyclopropanecarboxamide in water; after the combination of the substances mentioned, a post-reaction time of 45 minutes is added on, likewise at 0° C. After this, a 20 % strength sodium hydroxide solution is added with cooling and, after a further post-reaction time of 30 minutes, the reaction solution is at 45°-50° C. for 2 hours. Up to this point, at which only a storage-stable aqueous solution of cyclopropylamine is obtained, 4 hours pass. A 25-30 % strength aqueous solution of cyclopropylamine is obtained by working up by distillation. The degree of conversion is stated as 85-95%.

The relatively long total reaction time on the one hand and the side reactions occurring in spite of working at 0° C. on the other hand, which are manifested in decreased yields, indicate the difficulties of this process.

SUMMARY OF THE INVENTION

It has now been found that it brings considerable advantages if the cyclopropanecarboxamide is employed in the form of an aqueous solution instead of a suspension, although in this case a lower space yield has to be taken into account. Such a reaction procedure permits the use of a higher reaction temperature, by means of which the initially lower space yield is compensated for again by an increased time yield.

The present invention accordingly relates to a process for the preparation of cyclopropylamine by reaction of cyclopropanecarboxamide with alkali metal hypohalite in water as a reaction medium (Hofmann degradation) and subsequent treatment of the reaction mixture with alkali metal hydroxide, which is characterized in that the cyclopropanecarboxamide is employed in the form of a solution.

DETAILED DESCRIPTION OF THE INVENTION

The process according to the invention is carried out at 5°-35° C., preferably at 10°-25° C., and particularly preferably at 15°-20° C.

The reaction is carried out by addition of an in general stoichiometric amount of an alkali metal hypohalite. An alkali metal hypohalite which may be mentioned is, for example, sodium hypochlorite, sodium hypobromite, potassium hypochlorite and potassium hypobromite, preferably sodium hypochlorite.

In a preferred variant, it is furthermore possible, against the teaching of the prior art, to introduce the reaction mixture for the treatment with alkali metal hydroxide into a concentrated alkali metal hydroxide solution, instead of inversely adding the alkali metal hydroxide solution to the reaction mixture with cooling. In this case, the preferred variant according to the invention does not need to be cooled. An alkali metal hydroxide which may be mentioned is, for example, sodium hydroxide or potassium hydroxide, preferably sodium hydroxide. This variant for the introduction of the reaction mixture into a concentrated alkali metal hydroxide solution brings considerable advantages in working safety since the exothermic hydrolysis and elimination of $CO_2$ can always be controlled by the rate of introduction. The large excess of alkali metal hydroxide (for example 1.1–4 moles per role of amide, preferably 1.5–3 roles per role) furthermore leads to the reaction proceeding to completion, undesired side reactions being largely suppressed. In particular, undesired hydrolysis of acid amide is hardly observed, if at all.

Against the teaching of the art, it has thus been shown that, surprisingly, working at higher temperatures not only increases the working safety, but also suppresses side reactions and thus avoids decreased yields. To this end, the observation according to the invention that the process must be carried out in a homogeneous reaction system is important.

After introducing the reaction mixture into the concentrated alkali metal hydroxide solution, the cyclopropylamine is separated off by distillation from the mixture obtained in this case. Against the teaching of the prior art, in this case the largest part of the cyclopropylamine can be obtained in a largely anhydrous form (0.1–5 % by weight of water).

The largest part of the cyclopropylamine obtainable in nearly anhydrous form which may be mentioned is about 80–95 % of the total cyclopropylamine obtained. The remainder is obtained in the form of a cyclopropylamine/water distillate which can be fed back into the distillation or worked up separately to give relatively highly concentrated cyclopropylamine.

The reaction which can be carried out in the homogeneous phase in the process according to the invention also permits carrying out in continuously working apparatuses; in this case only small amounts of predominantly unstable solutions are always obtained, so that the working safety and the yield can be increased further with the continuous procedure.

EXAMPLE 1

299.6 g of 99.3 % strength cyclopropanecarboxamide were dissolved in 2100 g of water. 1954 g of 13.3 % strength NaOCl solution were metered in at 10–20° C. in the course of 40 minutes. After stirring for 1 hour at 20° C., this solution was transferred to a distillation apparatus, in which there were 1344 g of 50 % strength NaOH at 20° C. During pumping in, the temperature rose to about 70° C. and was subsequently brought to boiling point by additional heating.

From a bottom temperature of 88° C., cyclopropylamine of boiling point 49° C. was obtained. The bottom temperature rose continuously to 108° C., the head temperature rising very rapidly to about 98° C. after the recovery of the main portion of cyclopropylamine (about 80 % of the theoretical yield) and another aqueous cyclopropylamine solution (about 15 % of the theoretical yield) being obtained which could be distilled again in the next batch.

| Yield: | |
|---|---|
| (I) 164.3 g containing 1.5% of water = | 81.7% of the theoretical yield |
| (II) 675 g containing 28.2 g of cyclopropylamine = | 14.1% of the theoretical yield |
| | 95.8% of the theoretical yield |

Fraction I was obtained at a head temperature of 49°–50° C., fraction II at 50°–100° C.

EXAMPLE 2

An apparatus consisted of 2 stirring flasks and a separate distillation column with the customary equipment. Flask 1 was charged via 2 pumps with a cyclopropanecarboxamide solution and NaOCl solution. The contents of flask 1 were brought into flask 2 via an overflow; flask 2 was charged with sodium hydroxide solution via the 3rd pump.

After attaining the stationary state (forerun time of 15 minutes), the following quantities were made to react in the course of 30 min.:

171.7 g of 99 % strength cyclopropanecarboxamide, dissolved in 888.2 g of water, were pumped into the flask 1 at about 18° C. at the same time as 1069.6 g of 13.9 % NaOCl solution; the residence time was 6 minutes (residence time 1). The mixture resulting therefrom was then mixed in flask 2 together with 711.0 g of 45 % strength NaOH at temperatures below 30° C. and a residence time of 2.5 minutes (residence time 2) by means of a 3rd pump and collected in the distillation apparatus until the start of the batchwise distillation.

In the distillation, pure cyclopropylamine (b.p.: 49° C.) was obtained first, the water content of which was determined by means of the reflux ratio (reflux ratio of 1:1 gave about 2–3 % water content, reflux ratio of 3:1 gave about 1 % water content), before a water-containing fraction was obtained in the range from 50°–99° C., which at 99° C. still contained only about 1–2 % of cyclopropylamine.

Cyclopropylamine could be obtained from this fraction either by repeated precision distillation or, after adding HCl, isolated as the hydrochloride by stripping off the water.

Yield: 97.6 g of cyclopropylamine (CPA)=1.71 mol=85.5 % of the theoretical yield (isolated as 100.1 g of CPA having a 2.5 % water content, reflux ratio=1:1, boiling point 49° C.) and 24.9 g of CPA×HCl=0.26 mol=13.0 % of the theoretical yield (water-containing fraction, 50°–100° C.).

Total =98.5 % of the theoretical yield.

EXAMPLE 3

The apparatus used consisted of a reaction tube (350 ml volume) fitted with a premix device and cooling and 2 pumps for the addition of cyclopropanecarboxamide solution and NaOcl solution. A distillation apparatus was allocated, which contained the NaOH as an initial introduction (cooled to under 28° C.) and was equipped with a 60 cm packed column, adjusted to a reflux ratio of 1:1, a 4-ltr. 4-necked flask, a heating bath, an internal thermometer, a mechanical stirrer and an inlet tube.

171.7 g of 99 % strength cyclopropanecarboxamide, dissolved in 888.2 g of water, were at the same time mixed with 1047.0 g of 14.2 % strength NaOCl solution at a temperature of 14° C. and brought to reaction with a residence time of 4.25 min. (RT 1). The solution was then run into the cooled initial introduction of 711.0 g of 45 % strength NaOH, the temperature being kept below 25° C. by cooling.

Distillation and isolation of the product was carried out as in Example 2.

Yield: 100.6 g of CPA=1.77 mol=88.2 % of the theoretical yield (isolated as 104.2 g of CPA containing 3.5 % H₂O, reflux ratio 1:1, boiling point 49°–50° C.).
13.3 g of CPA×HCl=0.15 mol=7.1 % of theory
Total =95.5 % of theory

EXAMPLE 4 (for comparison)

The reaction was carried out analogously to Example 1, although the cyclopropanecarboxamide was not dissolved in water, but the reaction was carried out using a suspension: instead of 2100 g of water 700 g of water were used. Working up was carried out as in Example 1.

| Yield: | |
|---|---|
| (I) 129.1 g containing 1.3% of water = | 61.1% of theory |
| (II) 652 g containing 23.4 g of cyclopropylamine = | 11.7% of theory |
| | 72.8% of theory |

EXAMPLE 5

Example 5 was intended to be an example of the invention in the sense of the statement on p. 2.

The reaction was carried out analogously to Example 1, although the sodium hydroxide solution was metered into the reaction mixture and not the reaction mixture into the sodium hydroxide solution. Yield:

| Yield: | |
|---|---|
| (I) 148.1 g containing 1.9% of water = | 72.9% of theory |
| (II) 708 g containing 27.4 g of cyclopropylamine = | 13.7% of theory |
| | 86.5% of theory |

We claim:
1. A process for the preparation of cyclopropylamine by reaction of cyclopropanecarboxiamide with alkali metal hypohalite in water as reaction medium (Hofmann degradation) and subsequent treatment of the reaction mixture with alkali metal hydroxide, wherein the cyclopropanecarboxamide is employed in the form of a solution and wherein the reaction mixture for subsequent treatment with alkali metal hydroxide is introduced without cooling into an at least 45% alkali metal hydroxide solution.

2. The process of claim 1, wherein (the reaction is carried out at 5°–35° C.

3. The process of claim 2, wherein the reaction is carried out at 10°–25° C.

4. The process of claim 3, wherein the reaction is carried out at 5°–20° C.

5. The process of claim 1, wherein sodium hydroxide is employed as the alkali metal hydroxide.

6. The process of claim 1, wherein the reaction is carried out continuously.

* * * * *

UNITED STATES PATENT AND TRADEMARK OFFICE
CERTIFICATE OF CORRECTION

PATENT NO. : 5,032,687

DATED : July 16, 1991

INVENTOR(S) : Diehl et al.

It is certified that error appears in the above-identified patent and that said Letters Patent is hereby corrected as shown below:

Title Page  [73] Assignee: Delete " Kernforschunganlage Julich Gesellschaft mit beschrankter Haftung., Julich, Fed.Rep. of Germany "
and substitute -- Bayer Aktiengesellschaft, Leverkusen, Fed. Rep. of Germany --

Signed and Sealed this

Twentieth Day of April, 1993

*Attest:*

MICHAEL K. KIRK

*Attesting Officer*   Acting Commissioner of Patents and Trademarks